United States Patent
Eagle et al.

(10) Patent No.: US 10,531,799 B2
(45) Date of Patent: Jan. 14, 2020

(54) INTRAVENOUS ACCESS DEVICE DETECTING INTRAVENOUS INFILTRATION AND IN-VEIN PLACEMENT

(71) Applicant: Vanderbilt University, Nashville, TN (US)

(72) Inventors: Susan S. Eagle, Nashville, TN (US); Colleen Brophy, Nashville, TN (US); Kyle Mitchell Hocking, Nashville, TN (US); Franz Baudenbacher, Franklin, TN (US); Richard Boyer, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 96 days.

(21) Appl. No.: 15/547,935

(22) PCT Filed: Feb. 3, 2016

(86) PCT No.: PCT/US2016/016420
§ 371 (c)(1),
(2) Date: Aug. 1, 2017

(87) PCT Pub. No.: WO2016/126856
PCT Pub. Date: Aug. 11, 2016

(65) Prior Publication Data
US 2018/0020935 A1    Jan. 25, 2018

Related U.S. Application Data

(63) Continuation-in-part of application No. 14/853,504, filed on Sep. 14, 2015.
(Continued)

(51) Int. Cl.
*A61B 5/0215* (2006.01)
*A61M 5/172* (2006.01)
(Continued)

(52) U.S. Cl.
CPC ........ *A61B 5/02152* (2013.01); *A61B 5/7235* (2013.01); *A61M 5/158* (2013.01);
(Continued)

(58) Field of Classification Search
CPC .......... A61B 5/02152; A61M 5/16854; A61M 5/16859; A61M 5/16831; A61M 5/16836;
(Continued)

(56) References Cited

U.S. PATENT DOCUMENTS 3,693,612 A * 9/1972 Donahoe ............ A61B 5/02152
                                                      600/487
3,807,389 A * 4/1974 Miller ................ A61B 5/0215
                                                      600/487
(Continued)

FOREIGN PATENT DOCUMENTS

EP          0431310 A1    6/1991

OTHER PUBLICATIONS

Korean Intellectual Property Office (ISR/KR), "International Search Report for PCT/US2016/016420", Korea, dated May 16, 2016.
(Continued)

*Primary Examiner* — Meredith Weare
(74) *Attorney, Agent, or Firm* — Locke Lord LLP; Tim Tingkang Xia, Esq.

(57) ABSTRACT

Aspects of the invention relates to systems and methods for monitoring an intravenous (IV) line functionality of an IV device. In one embodiment, the system includes an IV catheter to be inserted into the vein of the living subject, at least one pressure sensor in fluid communication with the IV catheter to acquire peripheral venous signals; and a processing device. The processing device receives the peripheral venous signals from the pressure sensor, performs a spectral analysis on the peripheral venous signals to obtain a peripheral venous pressure frequency spectrum, and then performs
(Continued)

a statistical analysis on amplitudes of peaks of the peripheral venous pressure frequency spectrum to determine an IV line functionality of the IV catheter in real time. When the IV line functionality indicates IV infiltration, the processing device may control the fluid controlling device to stop the fluid flow from the fluid source to the IV catheter.

21 Claims, 12 Drawing Sheets

Related U.S. Application Data

(60) Provisional application No. 62/111,337, filed on Feb. 3, 2015.

(51) Int. Cl.
  *A61M 5/158* (2006.01)
  *A61M 5/168* (2006.01)
  *A61B 5/00* (2006.01)

(52) U.S. Cl.
  CPC ....... *A61M 5/16854* (2013.01); *A61B 5/7257* (2013.01); *A61M 2005/1588* (2013.01)

(58) Field of Classification Search
  CPC ............ A61M 5/1684; A61M 5/16845; A61M 2005/16863; A61M 2005/16868; A61M 2005/16872
  See application file for complete search history.

(56) References Cited

U.S. PATENT DOCUMENTS

| | | | | |
|---|---|---|---|---|
| 3,980,082 | A * | 9/1976 | Miller | A61B 5/0215 600/487 |
| 4,300,572 | A * | 11/1981 | Knighton | A61B 5/02152 600/486 |
| 4,648,869 | A | 3/1987 | Bobo, Jr. | |
| 4,898,576 | A | 2/1990 | Philip | |
| 4,959,050 | A * | 9/1990 | Bobo, Jr. | A61M 5/16859 128/DIG. 13 |
| 5,096,385 | A * | 3/1992 | Georgi | A61M 5/16859 417/18 |
| 5,122,731 | A * | 6/1992 | Cole | G01R 23/167 324/76.26 |
| 5,213,573 | A * | 5/1993 | Sorich | A61M 5/16859 128/DIG. 12 |
| 5,423,746 | A * | 6/1995 | Burkett | A61M 5/16859 128/DIG. 13 |
| 2003/0004492 | A1* | 1/2003 | Munis | A61B 5/021 604/503 |
| 2007/0112329 | A1* | 5/2007 | Sage, Jr. | A61M 5/16854 604/507 |
| 2009/0076400 | A1* | 3/2009 | Diab | A61B 5/14546 600/502 |
| 2011/0137241 | A1 | 6/2011 | Delcastilio et al. | |
| 2014/0073973 | A1 | 3/2014 | Sexton et al. | |
| 2014/0207062 | A1* | 7/2014 | Eagle | A61B 5/02141 604/111 |

OTHER PUBLICATIONS

European Patent Office, "Extended European Search Report for 16747218.2", The Hague, dated Jun. 11, 2018.

* cited by examiner

Central Venous Pressure (CVP)

Peripheral Venous Pressure (PVP)

| Cutoff | Sensitivity% | 95% CI | Specificity% | 95% CI | Likelihood ratio |
|---|---|---|---|---|---|
| < 2530 | 14.29 | 0.3610% to 57.87% | 100.0 | 59.04% to 100.0% | |
| < 4771 | 28.57 | 3.669% to 70.96% | 100.0 | 59.04% to 100.0% | |
| < 5176 | 42.86 | 9.899% to 81.59% | 100.0 | 59.04% to 100.0% | |
| < 6078 | 57.14 | 18.41% to 90.10% | 100.0 | 59.04% to 100.0% | |
| < 7073 | 71.43 | 29.04% to 96.33% | 100.0 | 59.04% to 100.0% | |
| < 7390 | 71.43 | 29.04% to 96.33% | 85.71 | 42.13% to 99.64% | 5.00 |
| < 8196 | 85.71 | 42.13% to 99.64% | 85.71 | 42.13% to 99.64% | 6.00 |
| < 9711 | 85.71 | 42.13% to 99.64% | 71.43 | 29.04% to 96.33% | 3.00 |
| < 12817 | 85.71 | 42.13% to 99.64% | 57.14 | 18.41% to 90.10% | 2.00 |
| < 18297 | 100.0 | 59.04% to 100.0% | 57.14 | 18.41% to 90.10% | 2.33 |
| < 23554 | 100.0 | 59.04% to 100.0% | 42.86 | 9.899% to 81.59% | 1.75 |
| < 25654 | 100.0 | 59.04% to 100.0% | 28.57 | 3.669% to 70.96% | 1.40 |
| < 108560 | 100.0 | 59.04% to 100.0% | 14.29 | 0.3610% to 57.87% | 1.17 |

| Cutoff | Sensitivity% | 95% CI | Specificity% | 95% CI | Likelihood ratio |
|---|---|---|---|---|---|
| > 7.500e-005 | 100.0 | 63.06% to 100.0% | 12.50 | 0.3160% to 52.65% | 1.14 |
| > 0.00015 | 100.0 | 63.06% to 100.0% | 25.00 | 3.185% to 65.09% | 1.33 |
| > 0.0016 | 100.0 | 63.06% to 100.0% | 37.50 | 8.523% to 75.51% | 1.60 |
| > 0.0060 | 100.0 | 63.06% to 100.0% | 50.00 | 15.70% to 84.30% | 2.00 |
| > 0.0095 | 100.0 | 63.06% to 100.0% | 62.50 | 24.49% to 91.48% | 2.67 |
| > 0.0120 | 100.0 | 63.06% to 100.0% | 75.00 | 34.91% to 96.81% | 4.00 |
| > 0.0150 | 87.50 | 47.35% to 99.68% | 75.00 | 34.91% to 96.81% | 3.50 |
| > 0.0169 | 87.50 | 47.35% to 99.68% | 87.50 | 47.35% to 99.68% | 7.00 |

INTRAVENOUS ACCESS DEVICE DETECTING INTRAVENOUS INFILTRATION AND IN-VEIN PLACEMENT

CROSS-REFERENCE TO RELATED PATENT APPLICATIONS

This PCT application claims the benefit, pursuant to 35 U.S.C. § 119(e), of U.S. provisional patent application Ser. No. 62/111,337, filed Feb. 3, 2015, entitled "INTRAVENOUS ACCESS DEVICE DETECTING INTRAVENOUS INFILTRATION AND IN-VEIN PLACEMENT," by Susan S. Eagle, Colleen Brophy, Kyle Mitchell Hocking, Franz Baudenbacher and Richard Boyer, the above disclosure of which is incorporated herein in its entireties by reference.

This PCT application is also a continuation-in-part of U.S. patent application Ser. No. 14/853,504, filed Sep. 14, 2015, entitled "HYPOVOLEMIA/HYPERVOLEMIA DETECTION USING PERIPHERAL INTRAVENOUS WAVEFORM ANALYSIS (PIVA) AND APPLICATIONS OF SAME," by Susan S. Eagle, Colleen Brophy, Kyle Mitchell Hocking, Franz Baudenbacher and Richard Boyer, which itself claims priority to and the benefit of, pursuant to 35 U.S.C. § 119(e), U.S. provisional patent application Serial No. U.S. provisional patent application Ser. No. 62/049,829, filed Sep. 12, 2014, entitled "METHOD FOR HARMONIC ANALYSIS OF PERIPHERAL VENOUS PRESSURE WAVEFORMS AND APPLICATIONS OF SAME," by Susan S. Eagle, Colleen Brophy, Kyle Mitchell Hocking, Franz Baudenbacher and Richard Boyer, all the above disclosures of which are incorporated herein in their entireties by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The present invention relates generally to intravenous (IV) therapy, and more specifically, the present invention relates to systems and methods for monitoring intravascular placement of an IV catheter and detecting IV infiltration, and applications of the same.

BACKGROUND OF THE INVENTION

While seemingly simple, proper intravascular placement of an intravenous (IV) catheter is mandatory for effective IV volume resuscitation and IV pharmacologic administration. Malpositioning or misplacing of IV catheters may occur at any time during hospitalization or when a patient is in a status under the potential need of IV volume resuscitation and/or IV pharmacologic administration. For example, ambulatory patients may inadvertently displace the catheter, often secured with tape; patients in the operating room setting often have their arms tucked in sheets, away from the operative field, precluding inspection of the IV insertion site for signs of infiltration; and pediatric patients often have IV catheters secured with devices to prevent patient tampering, which also obscures the IV insertion site.

Malpositioning of a peripheral IV catheter into the extravascular space precludes the patient from receiving necessary resuscitative therapy. Fluid administration into subcutaneous tissue or fascia may result in compartment syndrome and loss of the extremity. Tissue necrosis and gangrene may result from tissue infiltration of vasoactive medications.

Therefore, a heretofore unaddressed need exists in the art to address the aforementioned deficiencies and inadequacies.

SUMMARY OF THE INVENTION

In one aspect, the present invention relates to an intravenous (IV) system. In certain embodiments, the system includes: an IV catheter, configured to be inserted into a vein of a living subject; a fluid controlling device in fluid communication with the IV catheter, configured to control fluid flow from a fluid source to the IV catheter; at least one pressure sensor in fluid communication with the IV catheter, configured to acquire, from the vein of the living subject, peripheral venous signals; and a processing device communicatively connected to the at least one pressure sensor. The processing device is configured to: receive the peripheral venous signals from the at least one pressure sensor; perform a spectral analysis on the peripheral venous signals to obtain a peripheral venous pressure frequency spectrum; perform a statistical analysis on amplitudes of peaks of the peripheral venous pressure frequency spectrum to determine an IV line functionality of the IV catheter in real time, where the IV line functionality of the IV catheter indicates IV infiltration when amplitude decreases greater than a first threshold are detected from the peaks of the peripheral venous pressure frequency spectrum; and when the IV line functionality of the IV catheter indicates IV infiltration, control the fluid controlling device to stop the fluid flow from the fluid source to the IV catheter.

In certain embodiments, the IV infiltration indicates occlusion or malposition of the IV catheter.

In certain embodiments, the spectral analysis is a spectral fast Fourier transform (FFT) analysis.

In certain embodiments, the statistical analysis includes: obtaining a plurality of baseline peaks $\{B_{N-1}\}$ on a baseline peripheral venous pressure frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1} = B_{N-1}(F_{N-1})$, wherein $F_N$ is greater than $F_{N-1}$; obtaining a plurality of peaks $\{P_{N-1}\}$ on the peripheral venous pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1} = P_{N-1}(F_{N-1})$; and determining the IV line functionality in real time by comparing the amplitudes of the peaks $\{P_{N-1}\}$ to that of the baseline peaks $\{B_{N-1}\}$ respectively.

In certain embodiments, the baseline peripheral venous pressure frequency spectrum is obtained by: acquiring, by the at least one pressure sensor, the peripheral venous signals from the vein of the living subject at an earlier time period; and processing the peripheral venous signals acquired at the earlier time period by the spectral FFT analysis to obtain the baseline peripheral venous pressure frequency spectrum.

In certain embodiments, the IV system further includes: a tubing having a first end and an opposite, second end, wherein the first end is connectable to the fluid source, and the second end is connected to the IV catheter; and a port device in fluid communication with the tubing, located between the first and second ends of the tubing, where the at least one pressure sensor is in fluid communication with the tubing through the port device.

Another aspect of the present invention relates to an IV system, which includes an IV device and a processing device communicatively connected to the IV device. The IV device is configured to acquire, from a vein of a living subject, peripheral venous signals. The processing device is configured to: receive the peripheral venous signals from the IV device; perform a spectral analysis on the peripheral venous signals to obtain a peripheral venous pressure frequency spectrum; and perform a statistical analysis on amplitudes of peaks of the peripheral venous pressure frequency spectrum to determine an IV line functionality of the IV device in real time.

In certain embodiments, the processing device is a computing device.

In certain embodiments, the spectral analysis is a spectral FFT analysis.

In certain embodiments, the statistical analysis includes: obtaining a plurality of baseline peaks $\{B_{N-1}\}$ on a baseline peripheral venous pressure frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$; obtaining a plurality of peaks $\{P_{N-1}\}$ on the peripheral venous pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and determining the IV line functionality in real time by comparing the amplitudes of the peaks $\{P_{N-1}\}$ to that of the baseline peaks $\{B_{N-1}\}$ respectively.

In certain embodiments, the baseline peripheral venous pressure frequency spectrum is obtained by: acquiring, by the at least one pressure sensor, the peripheral venous signals from the vein of the living subject at an earlier time period; and processing the peripheral venous signals acquired at the earlier time period by the spectral FFT analysis to obtain the baseline peripheral venous pressure frequency spectrum.

In certain embodiments, the IV line functionality of the IV device is determined to indicate IV infiltration when amplitude decreases greater than a first threshold are detected from the peaks of the peripheral venous pressure frequency spectrum.

In certain embodiments, the IV device includes: an IV catheter, configured to be inserted into the vein of the living subject; a tubing having a first end and an opposite, second end, wherein the first end is connectable to a fluid source, and the second end is connected to the IV catheter; a port device in fluid communication with the tubing, located between the first and second ends of the tubing; and at least one pressure sensor in fluid communication with the tubing through the port device, configured to obtain the peripheral venous signals by measuring fluid pressures in the port device.

In certain embodiments, the IV infiltration indicates occlusion or malposition of the IV catheter.

In certain embodiments, the IV device further includes a fluid controlling device in fluid communication with the tubing, located between the first and second ends of the tubing to control fluid flow from the fluid source to the IV catheter. In certain embodiments, the processing device is further configured to, when the IV line functionality of the IV device is determined to indicate IV infiltration, control the fluid controlling device to stop the fluid flow from the fluid source to the IV catheter. Alternatively, the processing device is further configured to, when the IV line functionality of the IV device is determined to indicate IV infiltration, control the fluid controlling device to reduce a flow rate of the fluid flow from the fluid source to the IV catheter, or generate an alert message.

A further aspect of the present invention relates to a method for monitoring an IV line functionality of an IV device, which includes: acquiring, from an IV catheter, peripheral venous signals, wherein the IV catheter is configured to be inserted in a vein of the living subject; performing a spectral analysis on the acquired peripheral venous signals to obtain a peripheral venous pressure frequency spectrum; and performing a statistical analysis on amplitudes of peaks of the peripheral venous pressure frequency spectrum to determine the IV line functionality of the IV device in real time.

In certain embodiments, the spectral analysis is a spectral FFT analysis.

In certain embodiments, the statistical analysis includes: obtaining a plurality of baseline peaks $\{B_{N-1}\}$ on a baseline peripheral venous pressure frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$; obtaining a plurality of peaks $\{P_{N-1}\}$ on the peripheral venous pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and determining the IV line functionality in real time by comparing the amplitudes of the peaks $\{P_{N-1}\}$ to that of the baseline peaks $\{B_{N-1}\}$ respectively.

In certain embodiments, the baseline peripheral venous pressure frequency spectrum is obtained by: acquiring, by the at least one pressure sensor, the peripheral venous signals from the vein of the living subject at an earlier time period; and processing the peripheral venous signals acquired at the earlier time period by the spectral FFT analysis to obtain the baseline peripheral venous pressure frequency spectrum.

In certain embodiments, the IV line functionality of the IV device is determined to indicate IV infiltration when amplitude decreases greater than a first threshold are detected from the peaks of the peripheral venous pressure frequency spectrum.

In certain embodiments, the IV infiltration indicates occlusion or malposition of the IV catheter.

In certain embodiments, the IV device includes: an IV catheter, configured to be inserted into the vein of the living subject; a tubing having a first end and an opposite, second end, wherein the first end is connectable to a fluid source, and the second end is connected to the IV catheter; a port device in fluid communication with the tubing, located between the first and second ends of the tubing; at least one pressure sensor in fluid communication with the tubing through the port device, configured to obtain the peripheral venous signals by measuring fluid pressures in the port device; and a fluid controlling device in fluid communication with the tubing, located between the first and second ends of the tubing to control fluid flow from the fluid source to the IV catheter. In certain embodiments, the method further includes: when the IV line functionality of the IV device is determined to indicate IV infiltration, controlling the fluid controlling device to stop the fluid flow from the fluid source to the IV catheter.

In a further aspect, the present invention relates to a method for monitoring an intravenous (IV) line functionality of an IV device using the IV system as described above.

In certain embodiments, the system and method as described above may be used for monitoring and detecting IV infiltration in real time, thus preventing tissue damage to the patient.

These and other aspects of the present invention will become apparent from the following description of the preferred embodiments taken in conjunction with the following drawings, although variations and modifications thereof may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
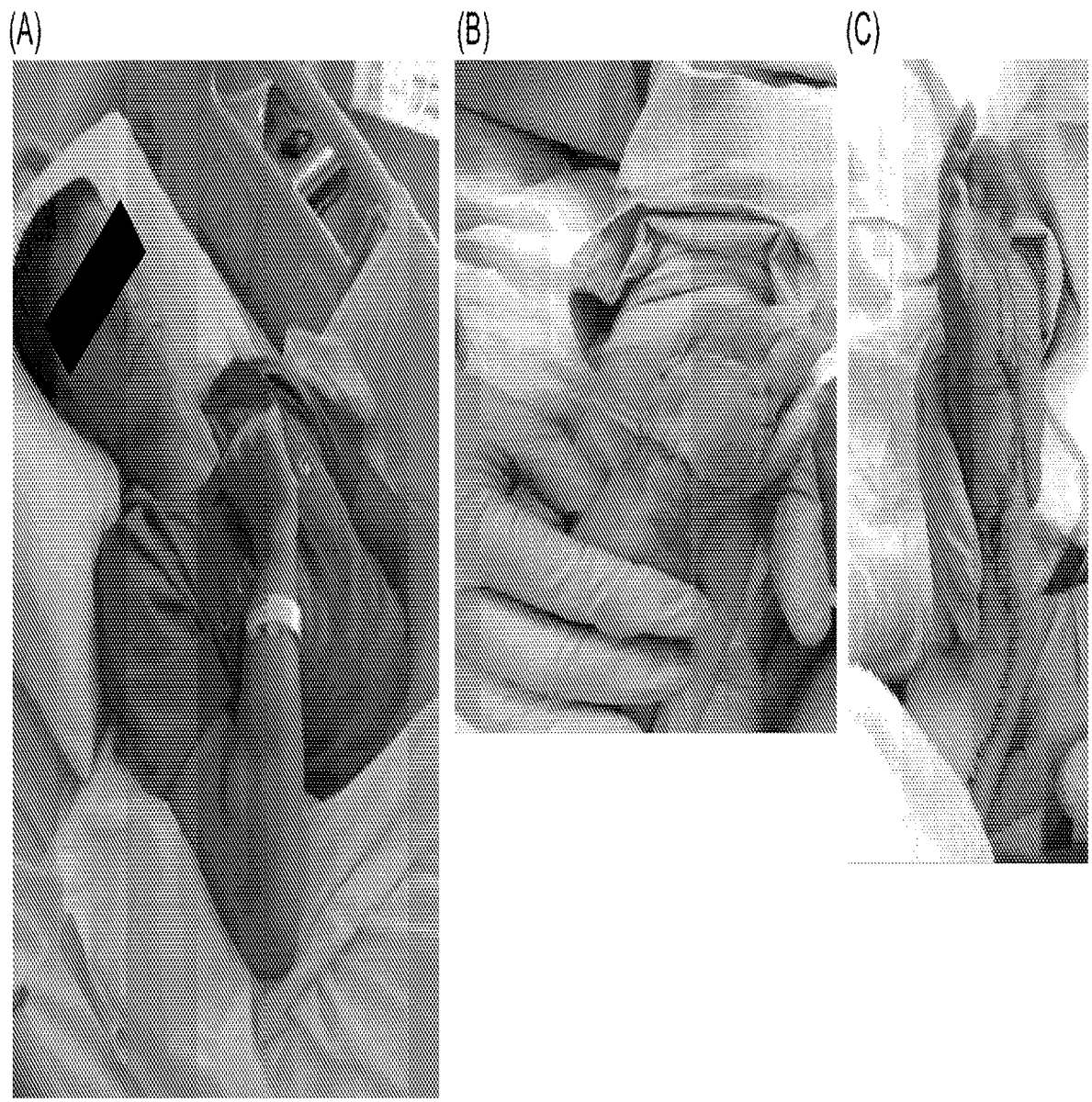
FIG. 1 shows patients in need of IV volume resuscitation according to certain embodiments of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower" can, therefore, encompass both an orientation of "lower" and "upper", depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the term "infiltration" refers to a medical condition where IV fluid leaks into surrounding tissues. Generally, IV infiltration may be commonly caused by improper placement or displacement of the IV catheter.

Patients with different injuries or diseases may require IV volume resuscitation and/or and IV pharmacologic administration. FIG. 1 shows patients in need of IV volume resuscitation according to certain embodiments of the present invention. As discussed above, malpositioning or misplacing of IV catheters may occur at any time for different patients to cause IV infiltration, which may be a major cause of morbidity and is difficult to detect. The economic burden caused by IV failures are costly. For example, the compartment syndrome and other medical symptoms resulted by IV failures may generate cost which must be absorbed by the hospitals and medical facilities. Further, patients and their family members may bring malpractice suits against the hospitals and medical professionals. It is estimated that over 50% of the medical malpractice claims are due to IV infiltration or extravasation, in comparison to other types of claims such as chemotherapy (~20%) and IV contrast (~0.7%). Further, there is no existing devices for ensuring proper IV catheter placement do not exist. Therefore, a need for IV devices and methods to ensure proper IV catheter placement is desired.

Figure 2A:
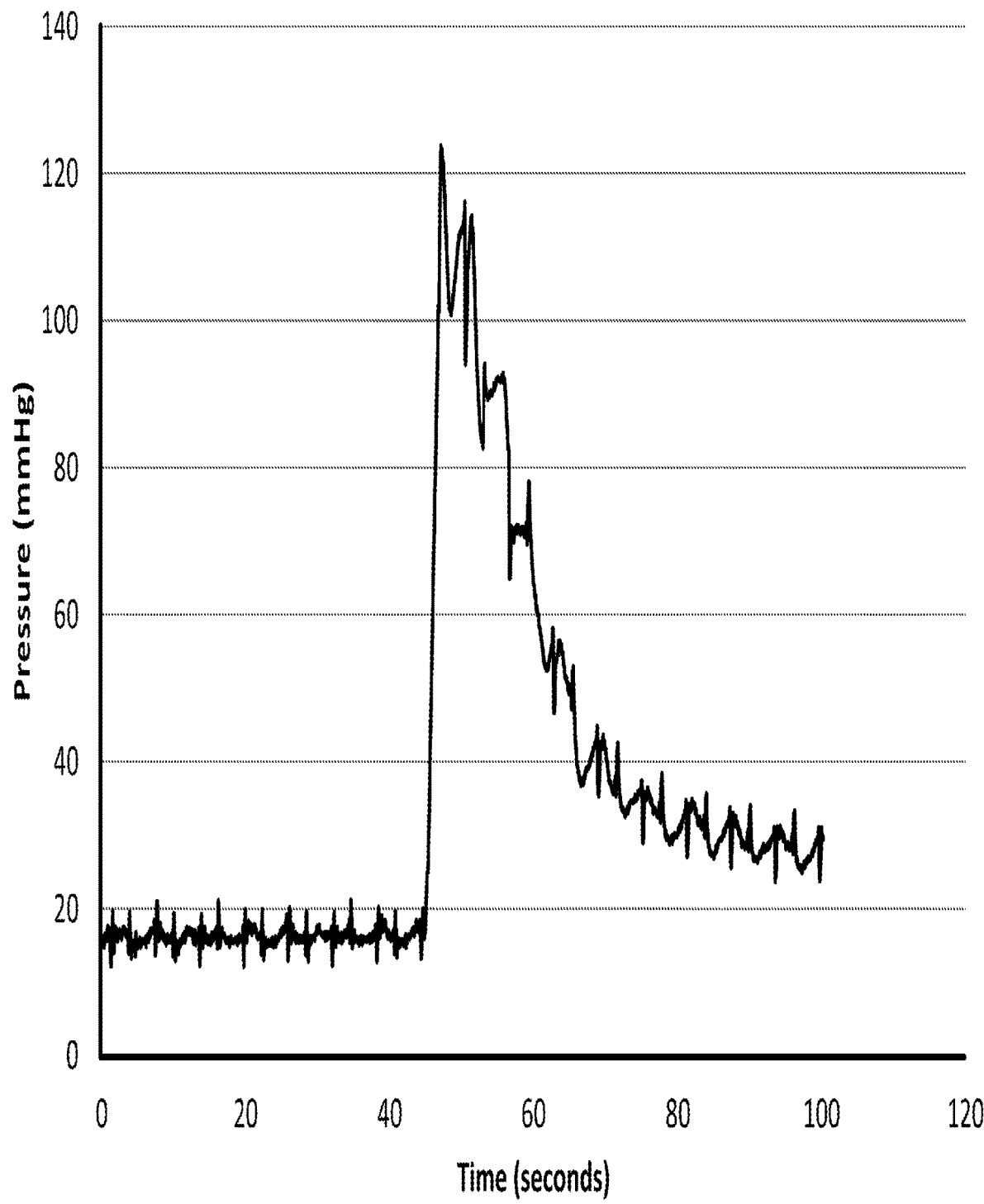
FIG. 2A shows a chart of line pressure of an IV tubing with pump flow at 50 mL/hour according to certain embodiments of the present invention.
Figure 2B:
FIG. 2B shows a result of IV infiltration for about 30 minutes according to certain embodiments of the present invention.

In certain embodiments, IV tubing may be coupled with pressure sensors to measure the average line pressure of the IV tubing. However, average line pressure is not an efficient parameter for detecting IV infiltration prior to tissue damage. FIG. 2A shows a chart of line pressure of an IV tubing with a pump flow at 50 mL/hour according to certain embodiments of the present invention. As shown in FIG. 2A, the average line pressure for a functional IV with a pump flow at 50 mL/hour is about 20 mmHg. When IV infiltration begins, the line pressure may go up to about 125 mmHg for a period of time. However, after about 30 minutes, the average line pressure for the infiltrated IV may be stabilized at a value of about 25 mmHg. At this point, detection of IV infiltration will be late as tissue damages have already occurred. FIG. 2B shows a result of IV infiltration for about 30 minutes according to certain embodiments of the present invention.

Accordingly, aspects of the present invention relates to systems and methods of monitoring intravascular placement of an IV catheter and detecting IV infiltration or misplacement on a living subject, which may include human beings and/or other animals, and applications of the same. In certain embodiments, the systems and methods may utilize a disposable IV tubing with independent or integrated venous pressure sensors, and durable dongle for wireless connectivity and pump interfacing. In certain embodiments, a proprietary spectral waveform analysis may be performed for confirming IV placement. The systems and methods may implement rapid infiltration detection.

In one aspect, the present invention relates to an intravenous (IV) system. In certain embodiments, the system includes: an IV catheter, configured to be inserted into a vein of a living subject; a fluid controlling device in fluid communication with the IV catheter, configured to control fluid flow from a fluid source to the IV catheter; at least one pressure sensor in fluid communication with the IV catheter, configured to acquire, from the vein of the living subject, peripheral venous signals; and a processing device communicatively connected to the at least one pressure sensor. The processing device is configured to: receive the peripheral venous signals from the at least one pressure sensor; perform a spectral analysis on the peripheral venous signals to obtain a peripheral venous pressure frequency spectrum; perform a statistical analysis on amplitudes of peaks of the peripheral venous pressure frequency spectrum to determine an IV line functionality of the IV catheter in real time, where the IV line functionality of the IV catheter indicates IV infiltration when amplitude decreases greater than a first threshold are detected from the peaks of the peripheral venous pressure frequency spectrum; and when the IV line functionality of the IV catheter indicates IV infiltration, control the fluid controlling device to stop the fluid flow from the fluid source to the IV catheter. Alternatively, the processing device may be further configured to, when the IV line functionality of the IV device is determined to indicate IV infiltration, control the fluid controlling device to reduce a flow rate of the fluid flow from the fluid source to the IV catheter, or generate an alert message.

A further aspect of the present invention relates to a method for monitoring an IV line functionality of an IV device, which includes: acquiring, from an IV catheter, peripheral venous signals, wherein the IV catheter is configured to be inserted in a vein of the living subject; performing a spectral analysis on the acquired peripheral venous signals to obtain a peripheral venous pressure frequency spectrum; and performing a statistical analysis on amplitudes of peaks of the peripheral venous pressure frequency spectrum to determine the IV line functionality of the IV device in real time.

Figure 3A:
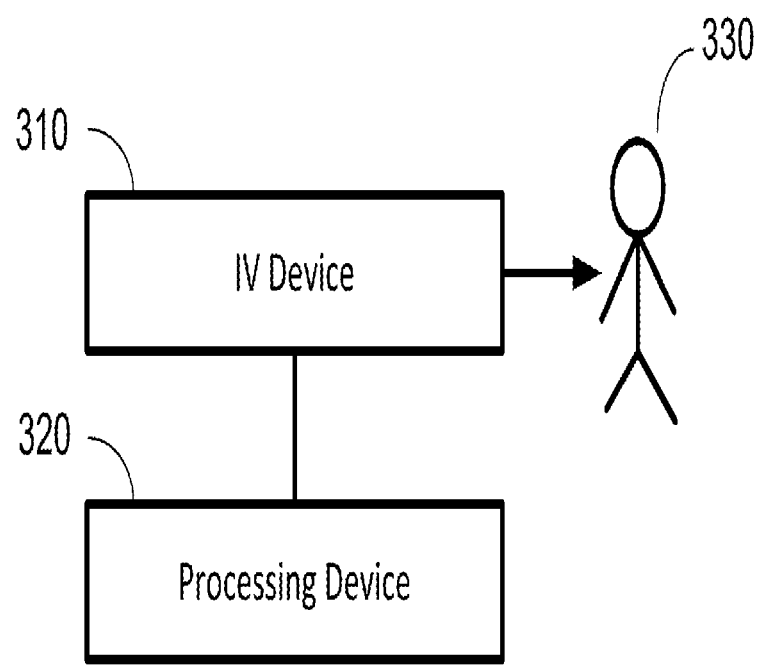
FIG. 3A shows an IV system according to certain embodiments of the present invention.

FIG. 3A shows an IV system according to certain embodiments of the present invention. As shown in FIG. 3A, the IV system 300 includes: an IV device 310 and a processing device 320. The processing device 320 is communicatively connected to the IV device 310. In certain embodiments, the connection between the IV device 310 and the processing device 320 may be through a network, which may be implemented by a wired connection or a wireless connection. Examples of the network may include without being limited to, a local area network (LAN), a wide area network (WAN), the Internet, or any other types of network.

The IV device 310 is configured to acquire, from a vein of a living subject 330, peripheral venous signals. In certain embodiments, the living subject may be a human being, or may be other animals. In one embodiment, the living subject may be a human patient who is given fluid through the IV device 310.

Figure 3B:
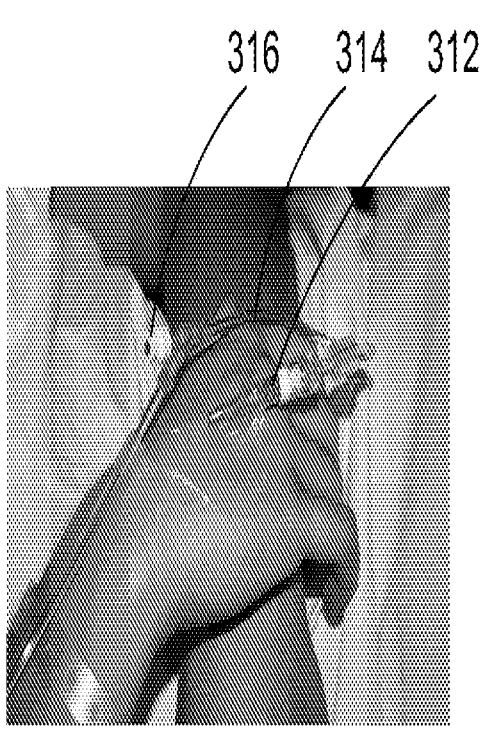
FIG. 3B shows an IV device according to certain embodiments of the present invention.
Figure 3C:
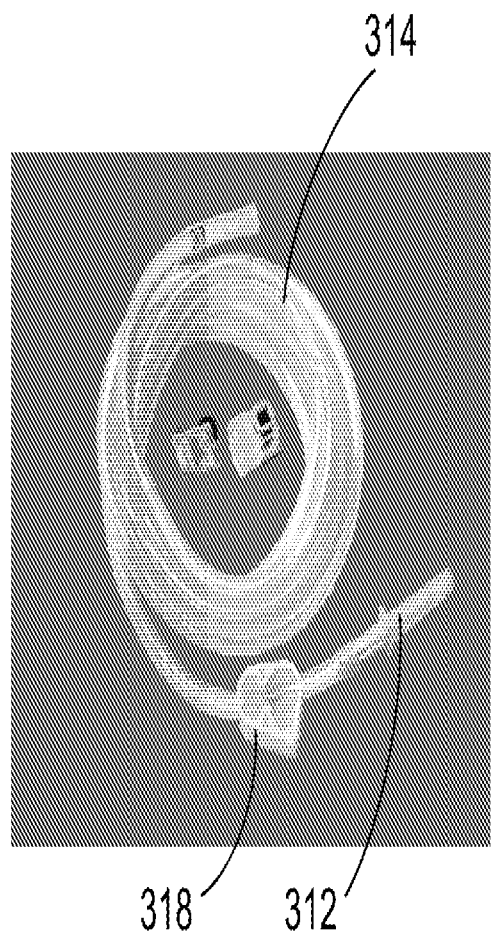
FIG. 3C shows an IV device according to certain embodiments of the present invention.

FIGS. 3B and 3C shows IV devices according to certain embodiments of the present invention. In certain embodiments, the IV device 310 may include an IV catheter 312, a tubing 314, a port device 316 and a fluid controlling device 318. In certain embodiments, the IV device 310 may include at least one pressure sensor (not shown). The IV catheter 312 is used to be inserted into the vein of the living subject 330 such that fluid may be supplied into the vein. The tubing 314 has a first end and an opposite, second end, where the first end is connectable to a fluid source (not shown) supplying the fluid, and the second end is connected to the IV catheter 312. The port device 316 is in fluid communication with the tubing 314, and located between the first and second ends of the tubing 314. In one embodiment, the port device 316 may include a T-piece or Y-piece connector. The fluid controlling device 318 is in fluid communication with the tubing 314, located between the first and second ends of the tubing 314 and configured to have an on position and an off position to control the fluid flow from the fluid source to the IV catheter 312. The at least one pressure sensor may be in fluid communication with the tubing 314 through the port device 316, for obtaining the peripheral venous signals by measuring fluid pressures in the port device 316. In operation, when the fluid controlling device 318 is in the on position, fluid flow in the tubing 314 is allowed to pass through the fluid controlling device 318, such that the at least one pressure sensor measures both a fluid pressure from the fluid source and a distal venous pressure from the vein, and when the fluid controlling device 318 is in the off position, no fluid flow in the tubing 314 is allowed to pass through the fluid controlling device 318, such that the at least one pressure sensor measures the distal venous pressure from the vein only. In certain embodiments, the fluid controlling device 318 may be manually or automatically controllable. In one embodiment, the fluid controlling device 318 may include a stopcock. In another embodiment, the fluid controlling device 318 includes an intravascular line occlusion mechanism, which may be manual or automatic. In certain embodiments, the at least one pressure sensor may include a pressure transducer, such that the peripheral venous signals are captured and recorded by the pressure transducer.

The processing device 320 is configured to: receive the peripheral venous signals from the IV device 310; perform a spectral analysis on the peripheral venous signals to obtain a peripheral venous pressure frequency spectrum in order to determine an IV line functionality of the IV device 310; and perform a statistical analysis on amplitudes of peaks of the peripheral venous pressure frequency spectrum to determine an IV line functionality of the IV device 310 in real time. In certain embodiments, the processing device 320 may be a computing device, which may be a desktop computer, a laptop computer, a smartphone, a tablet device, or any other computing devices with processors to perform the processing functions. In certain embodiments, the processor may be associated with a circuit board of data acquisition and process. In one embodiment, the processing device 320 may further include a display device (not shown) in communication with the processor for displaying the processed fluid pressures, and the display device may include a graphic interface. In certain embodiments, the spectral analysis may be a spectral fast Fourier transform (FFT) analysis. In certain embodiments, the spectral analysis may be other frequency and/or k-space transformation analysis.

Figure 4:
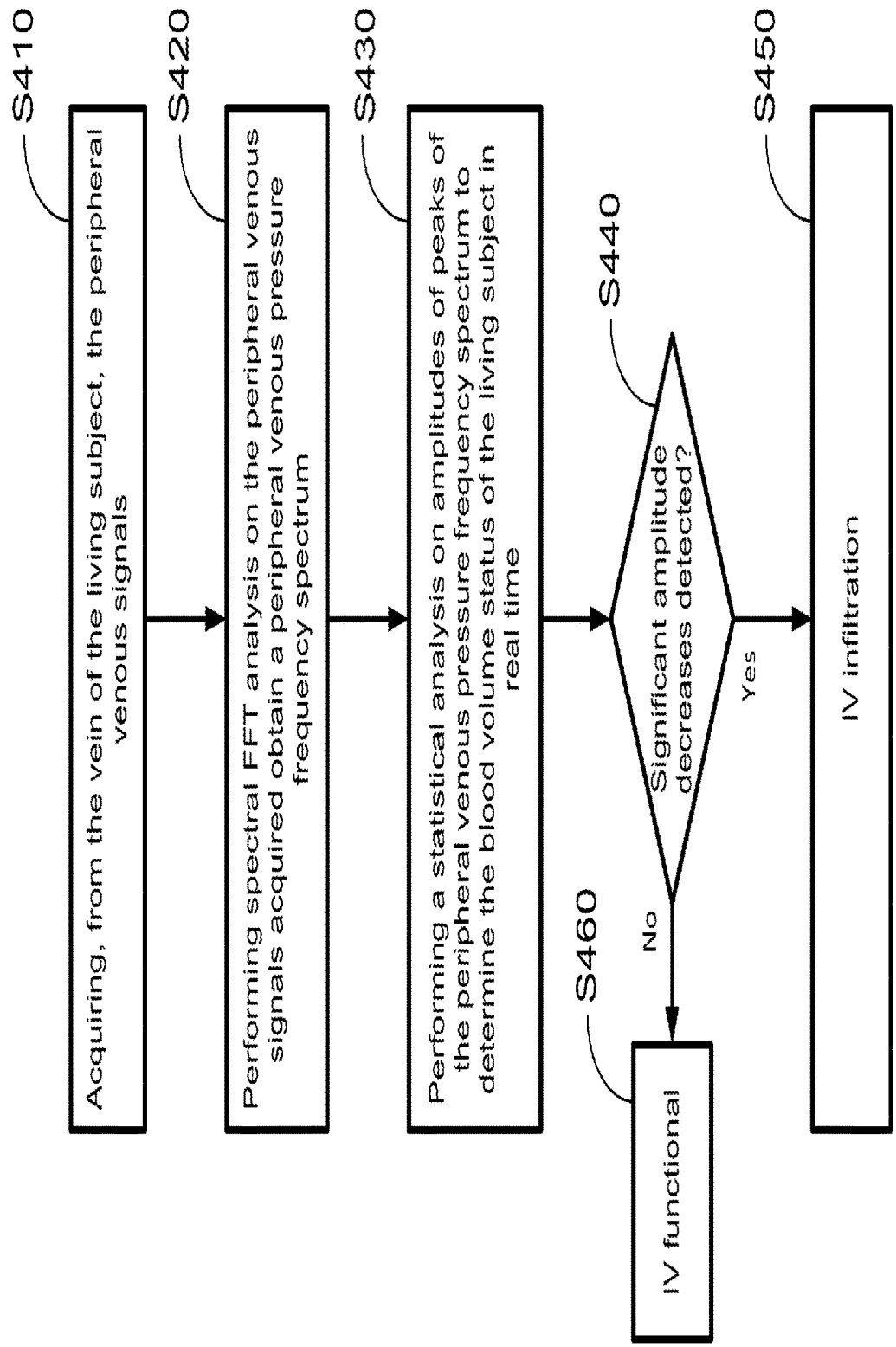
FIG. 4 shows a flowchart of a method for monitoring an IV line functionality of an IV device according to certain embodiments of the present invention.

FIG. 4 shows a flowchart of a method for monitoring an IV line functionality of an IV device according to certain embodiments of the present invention. As shown in FIG. 4, at step S410, the IV device 310 acquires the peripheral venous signals from the vein of the living subject. At step S420, upon receiving the peripheral venous signals from the IV device 310, the processing device 320 performs a spectral process and analysis, such as the spectral FFT analysis, on the peripheral venous signal to obtain a peripheral venous pressure frequency spectrum. At step S430, the processing device 320 performs a statistical analysis on amplitudes of peaks of the peripheral venous pressure frequency spectrum to determine the blood volume status of the living subject in real time. At step S440, the processing device 320 determines whether a significant amplitude decrease of the peaks is detected. If so, at step S450, the processing device 320 determines that IV infiltration occurs. If not, at step S460, the processing device 320 determines that no IV infiltration occurs (meaning that IV is functional).

Figure 5:
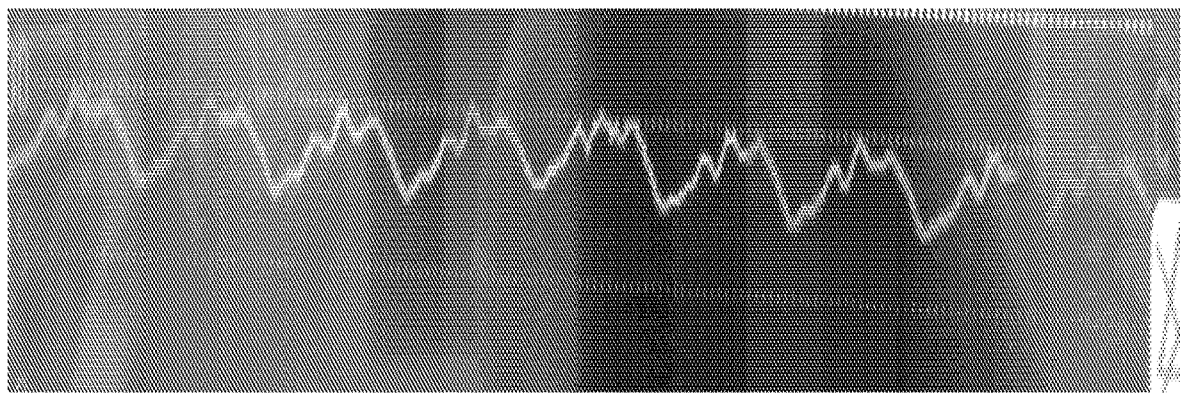
FIG. 5 shows comparison of central venous pressure (CVP) and peripheral venous pressure (PVP) according to certain embodiments of the present invention.
Figure 5:
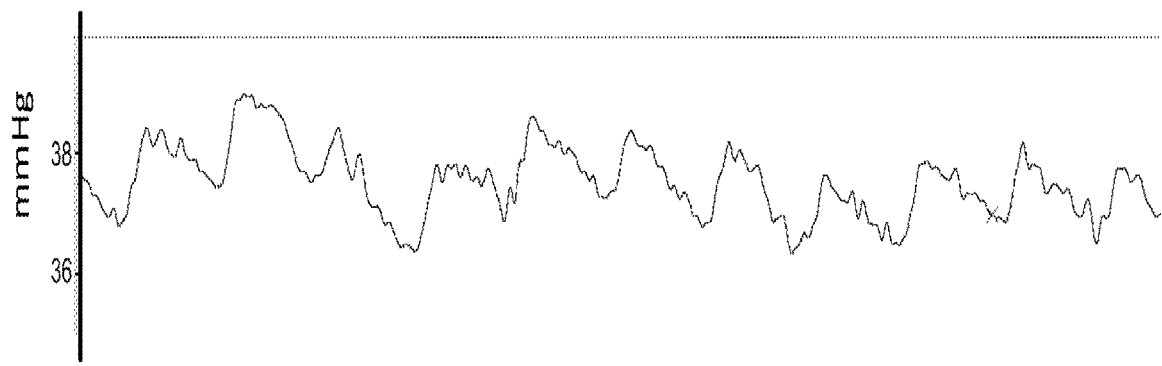

Generally, peripheral venous pressure (PVP) is strongly correlated with central venous pressure (CVP), also known as mean venous pressure (MVP), which is the pressure of blood in the thoracic vena cava, near the right atrium of the heart. FIG. 5 shows comparison of CVP and PVP according to certain embodiments of the present invention.

Figure 6:
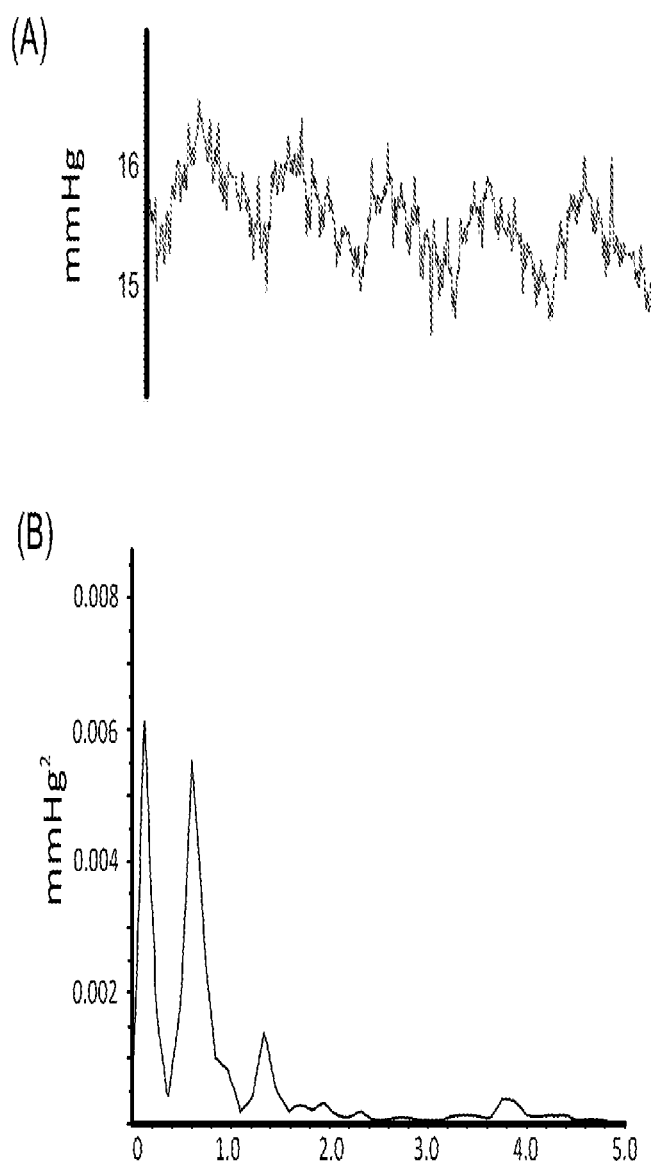
FIG. 6 shows (A) a chart of the peripheral venous waveforms and (B) the Fourier transformation of the signals according to certain embodiments of the present invention.

FIG. 6 shows (A) a chart of the peripheral venous waveforms and (B) the Fourier transformation of the signals according to certain embodiments of the present invention. As discussed above, line pressure sensing is insufficient for detecting venous access placement. In other words, merely using pumps and pressure sensors is not suitable to reliably detect IV infiltration. However, the IV systems and method as disclosed above may be used to detect and analyze the venous waveforms in order to efficiently monitor and detect IV infiltration. This is mainly due to the low venous signal-to-noise of the venous waveforms, which necessitates signal conditioning and spectral methods for analysis.

Figure 7:
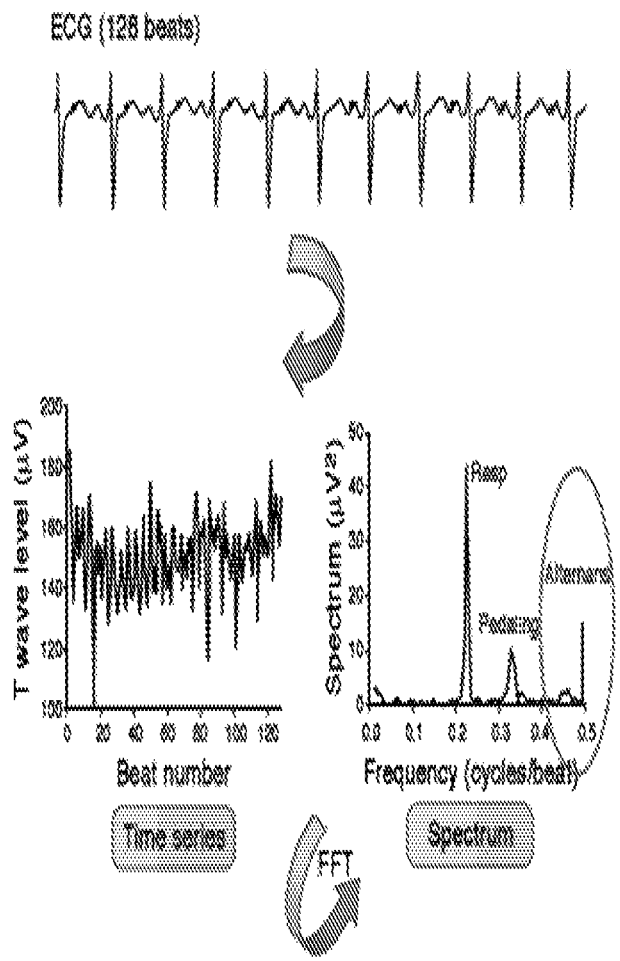
FIG. 7 shows the conversion from the peripheral venous signals to the peripheral venous pressure frequency spectrum according to certain embodiments of the present invention.

FFT separates the signals into the contributing frequencies. The amplitudes of the contributing frequencies in the signals can then be plotted and evaluated. FIG. 7 shows the conversion from the peripheral venous signals to the peripheral venous pressure frequency spectrum according to certain embodiments of the present invention. As shown in FIG. 7, an electrocardiogram (ECG) of 128 beats may be converted to T-wave alternans that can be evaluated with a FFT.

In certain embodiments, the steps S410 and S420 as shown in FIG. 4 may be performed continuously, such that at two different time period, two sets of the peripheral venous pressure frequency spectrums may be obtained. For example, for a time period from $T_0$ to $T_2$, the time period may be divided into a first time period from $T_0$ to $T_1$, and a second time period from $T_1$ to $T_2$, and each of the first time period and the second time period may be used to obtain a separate set of peripheral venous pressure frequency spectrums. In certain embodiments, the time period may be divided into more than two time periods, and multiple sets of peripheral venous pressure frequency spectrums may be obtained. In certain embodiments, the peripheral venous pressure frequency spectrum obtained at an earlier time may be used as a baseline peripheral venous pressure frequency spectrum. Thus, the statistical analysis at step S430 may be performed by obtaining a plurality of baseline peaks from a lower frequency side on a baseline peripheral venous pressure frequency spectrum, where N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=(F_{N-1})$, wherein $F_N$ is greater than $F_{N-1}$. In other words, the baseline peaks may include a first baseline peak $B_0$ corresponding to a first frequency $F_0$, a second baseline peak $B_1$ corresponding to a second frequency $F_1$, a third baseline peak $B_2$ corresponding to a third frequency $F_2$ . . . , and the second frequency $F_1$ is greater than the first frequency $F_0$. Then, a plurality of peaks $\{P_{N-1}\}$ may be obtained on the peripheral venous pressure frequency spectrum currently obtained, where the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}$ ($F_{N4}$). For example, the peaks may include a first peak $P_0$ corresponding to the first frequency $F_0$, a second peak $P_1$ corresponding to the second frequency $F_1$, a third peak $P_2$ corresponding to the third frequency $F_2$ . . . . In certain embodiments, the number of peaks on the peripheral venous pressure frequency spectrum equals to the number of baseline peaks on the baseline peripheral venous pressure frequency spectrum. In this way, the IV line functionality of the IV device 310 may be determined in real time by comparing the amplitudes of the peaks to that of the corresponding baseline peaks, respectively.

Figure 8:
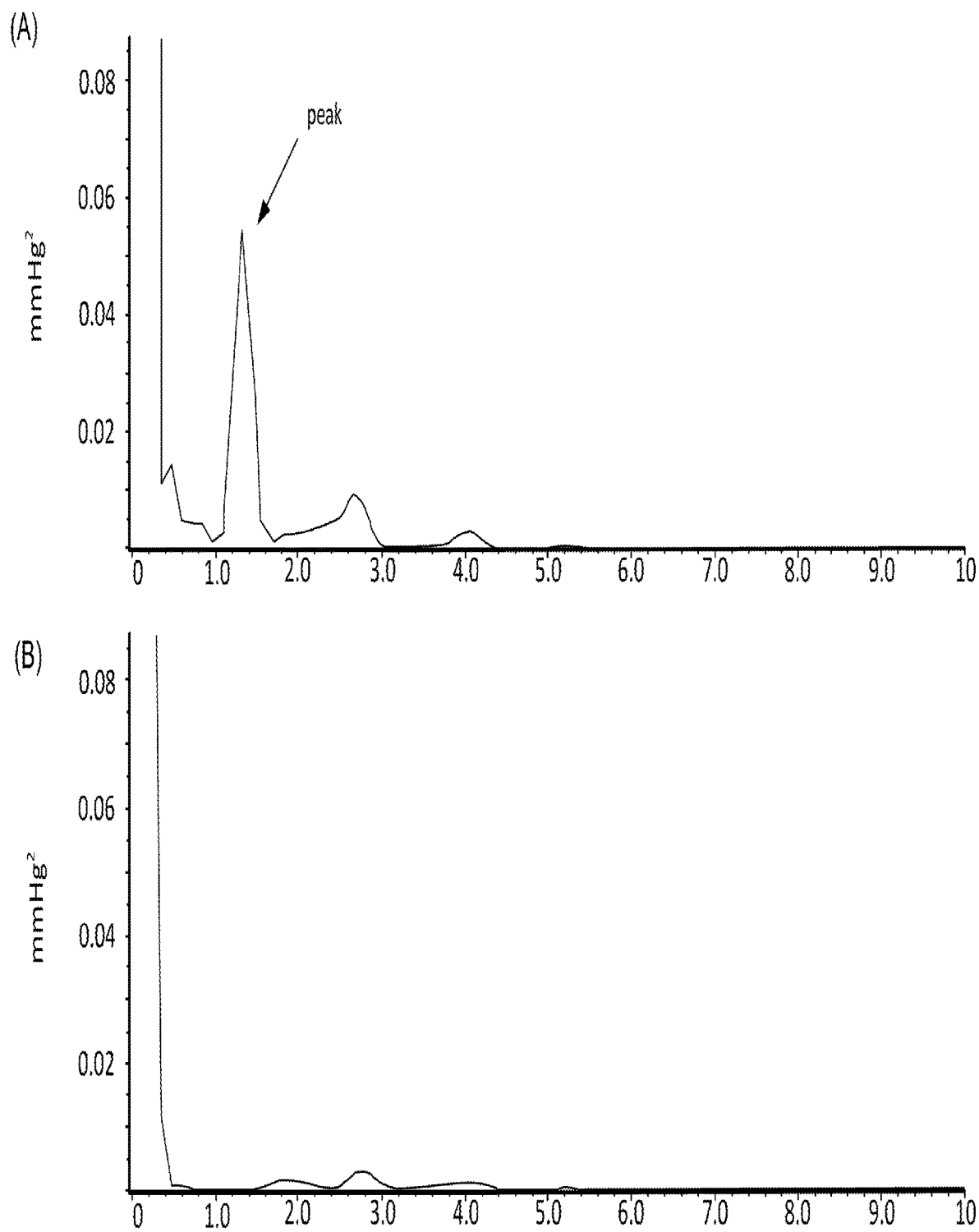
FIG. 8 shows the peripheral venous pressure frequency spectrum of (A) a functional IV and (B) an infiltrated IV according to certain embodiments of the present invention.

In certain embodiments, the IV line functionality of the IV catheter is determined to indicate IV infiltration when amplitude decreases greater than a first threshold are detected from the baseline peaks $\{B_{N-1}\}$ to the peaks $\{P_{N-1}\}$. FIG. 8 shows the peripheral venous pressure frequency spectrum of (A) a functional IV and (B) an infiltrated IV according to certain embodiments of the present invention. As shown in FIG. 8(A), when IV performs functionally, the amplitudes of the peaks of the peripheral venous pressure frequency spectrum do not show any significant decrease. In comparison, when IV infiltration occurs, as shown in FIG. 8(B), the amplitudes of the peaks of the peripheral venous pressure frequency spectrum decrease significantly. If the decrease reaches the first threshold, the processing device 120 will determine that IV infiltration has occurred in the living subject.

In certain embodiments, in addition to performing the statistical analysis on the amplitudes of peaks of the peripheral venous pressure frequency spectrum, the system and method may further utilize other features, such as performing mathematical operations or transformations to obtain power peaks of the peripheral venous pressure frequency spectrum to perform the statistical analysis. For example, the system and method may perform a mathematical operation for squaring the magnitude of the signal in order to obtain the power peaks of the peripheral venous pressure frequency spectrum, and then use the power peaks to conduct the statistical analysis.

In certain embodiments, when the IV line functionality of the IV catheter is determined to indicate IV infiltration, the processing device 320 may perform actions to avoid injuries that may be caused by the IV infiltration, where the action may be determined based on the nature of the IV therapy and the condition of the patient. For example, the processing device 320 may control the fluid controlling device 318 to stop the fluid flow from the fluid source to the IV catheter 312. Alternatively, the processing device 320 may control the fluid controlling device 318 to reduce a flow rate of the fluid flow from the fluid source to the IV catheter 312. In another example, the processing device 320 may generate an alert message to notify the medical professionals about the IV infiltration.

The inventors have utilized the systems and methods as discussed above in different models as a plurality of examples, including a human being model (n=6) for linear SSE analysis and a porcine model (n=8) for spectral analysis, to analyze and study the sensitivity and specificity of shifts in the peripheral venous waveforms. The tests in the examples are performed in standardized settings in order to test the hypothesis that the systems and methods are is more sensitive and specific than standard and invasive line pressure sensing of IV filtration.

Figures 9A, 9B:
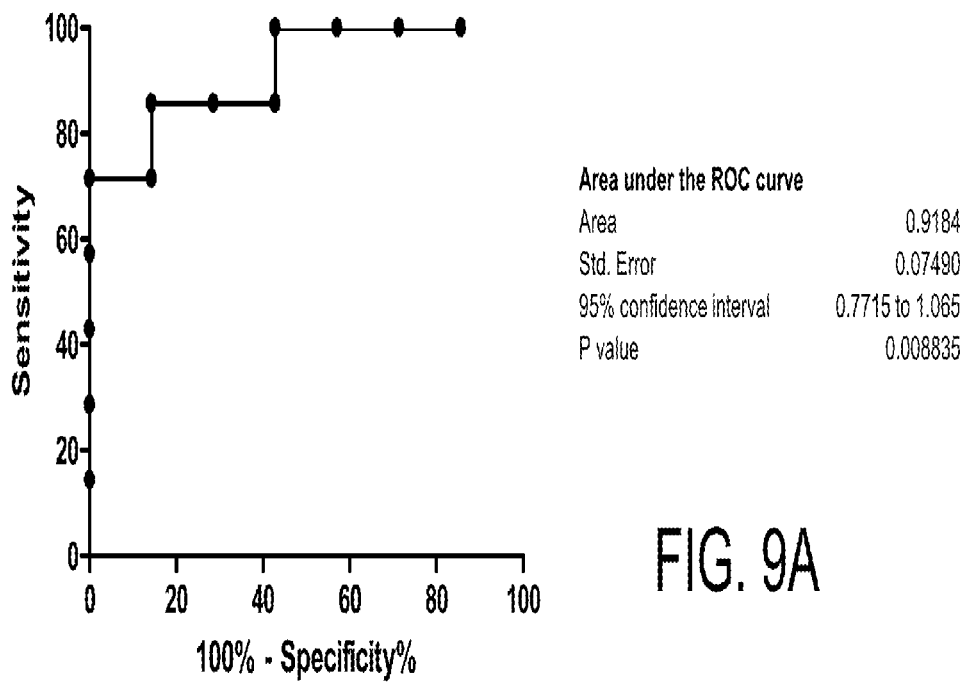
FIG. 9A shows the ROC curves for detection of linear SSE analysis on human beings according to certain embodiments of the present invention.
FIG. 9B shows a table of the ROC curves and 95% confidence interval (CI) for the data as shown in FIG. 9A according to certain embodiments of the present invention.

FIG. 9A shows the ROC curves for detection of linear SSE analysis on human beings according to certain embodiments of the present invention. FIG. 9B shows a table of the ROC curves and 95% confidence interval (CI) for the data as shown in FIG. 9A according to certain embodiments of the present invention. As shown in FIGS. 9A and 9B, the ROC curve is generated with an area under the curve (AUC) of 0.9184, the standard error is 0.07490, and the 95% CI is from 0.7715 to 1.065.

Figures 10A, 10B:
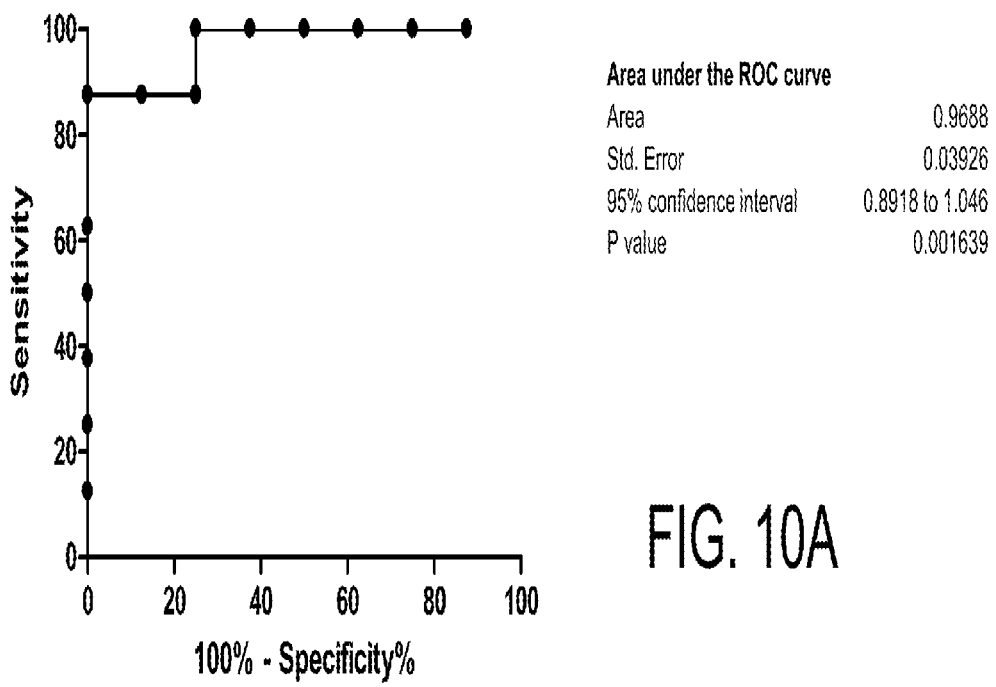
FIG. 10A shows the ROC curves for spectral analysis on porcines according to certain embodiments of the present invention.
FIG. 10B shows a table of the ROC curves and 95% confidence interval (CI) for the data as shown in FIG. 10A according to certain embodiments of the present invention.

FIG. 10A shows the ROC curves for spectral analysis on porcines according to certain embodiments of the present invention. FIG. 10B shows a table of the ROC curves and 95% confidence interval (CI) for the data as shown in FIG. 10A according to certain embodiments of the present invention. As shown in FIGS. 10A and 10B, the ROC curve is generated with an area under the curve (AUC) of 0.9688, the standard error is 0.03926, and the 95% CI is from 0.8918 to 1.046.

In certain embodiment, the data undergoes the Fourier transform and a physiologic signal associated with the same frequency (e.g. heart rate) is used to determine proper line placement.

The invention relates to systems and methods for monitoring and detecting IV infiltration using peripheral venous pressure analysis algorithm, t, and its applications. In certain aspects, the invention recites, among other things:

1) Harmonic peripheral venous pressure waveform analysis algorithm.
2) Method of measuring peripheral venous pressure frequency spectra for determination of real-time IV infiltration.
3) A venous pressure monitor algorithm that can distinguish between functional IV and infiltrated IV (which may be caused by IV malpositioning or misplacement).
4) A closed loop system for controlling IV fluid supply with a peripheral venous pressure monitor and intravenous fluid pump.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An intravenous (IV) system, comprising:
   an IV catheter, configured to be inserted into a vein of a living subject;
   a fluid controlling device in fluid communication with the IV catheter, configured to control fluid flow from a fluid source to the IV catheter;
   at least one pressure sensor in fluid communication with the IV catheter, configured to acquire, from the vein of the living subject, peripheral venous signals; and
   a processing device communicatively connected to the at least one pressure sensor, configured to:
   receive the peripheral venous signals from the at least one pressure sensor;
   perform a spectral analysis on the peripheral venous signals to obtain a peripheral venous pressure frequency spectrum;
   perform a statistical analysis on amplitudes of peaks of the peripheral venous pressure frequency spectrum to determine an IV line functionality of the IV catheter in real time, wherein the IV line functionality of the IV catheter indicates IV infiltration when amplitude decreases greater than a first threshold are detected from the peaks of the peripheral venous pressure frequency spectrum; and
   when the IV line functionality of the IV catheter indicates IV infiltration, control the fluid controlling device to stop the fluid flow from the fluid source to the IV catheter.

2. The system of claim 1, wherein the IV infiltration indicates occlusion or malposition of the IV catheter.

3. The system of claim 1, wherein the spectral analysis is a spectral fast Fourier transform (FFT) analysis.

4. The system of claim 3, wherein the statistical analysis comprises:
   obtaining a plurality of baseline peaks $\{B_{N-1}\}$ on a baseline peripheral venous pressure frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$;
   obtaining a plurality of peaks $\{P_{N-1}\}$ on the peripheral venous pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and
   determining the IV line functionality in real time by comparing the amplitudes of the peaks $\{P_{N-1}\}$ to that of the baseline peaks $\{B_{N-1}\}$ respectively.

5. The system of claim 4, wherein the baseline peripheral venous pressure frequency spectrum is obtained by:
   acquiring, by the at least one pressure sensor, the peripheral venous signals from the vein of the living subject at an earlier time period; and
   processing the peripheral venous signals acquired at the earlier time period by the spectral FFT analysis to obtain the baseline peripheral venous pressure frequency spectrum.

6. The system of claim 1, further comprising:
   a tubing having a first end and an opposite, second end, wherein the first end is connectable to the fluid source, and the second end is connected to the IV catheter; and
   a port device in fluid communication with the tubing, located between the first and second ends of the tubing;
   wherein the at least one pressure sensor is in fluid communication with the tubing through the port device.

7. An intravenous (IV) system, comprising:
   an IV device configured to acquire, from a vein of a living subject, peripheral venous signals; and
   a processing device communicatively connected to the IV device, configured to:
   receive the peripheral venous signals from the IV device;
   perform a spectral analysis on the peripheral venous signals to obtain a peripheral venous pressure frequency spectrum; and
   perform a statistical analysis on amplitudes of peaks of the peripheral venous pressure frequency spectrum to determine an IV line functionality of the IV device in real time, wherein the IV line functionality of the IV device is determined to indicate IV infiltration when amplitude decreases greater than a first threshold are detected from the peaks of the peripheral venous pressure frequency spectrum,
   wherein the IV device comprises:
   an IV catheter, configured to be inserted into the vein of the living subject;
   a tubing having a first end and an opposite, second end, wherein the first end is connectable to a fluid source, and the second end is connected to the IV catheter; and
   a fluid controlling device in fluid communication with the tubing, located between the first and second ends of the tubing to control fluid flow from the fluid source to the IV catheter,
   wherein the processing device is further configured to, when the IV line functionality of the IV device is determined to indicate IV infiltration, control the fluid controlling device to stop the fluid flow from the fluid source to the IV catheter.

8. The system of claim 7, wherein the processing device is a computing device.

9. The system of claim 7, wherein the spectral analysis is a spectral fast Fourier transform (FFT) analysis.

10. The system of claim 9, wherein the statistical analysis comprises:
    obtaining a plurality of baseline peaks $\{B_{N-1}\}$ on a baseline peripheral venous pressure frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$;
    obtaining a plurality of peaks $\{P_{N-1}\}$ on the peripheral venous pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and
    determining the IV line functionality of the IV device in real time by comparing the amplitudes of the peaks $\{P_{N-1}\}$ to that of the baseline peaks $\{B_{N-1}\}$ respectively.

11. The system of claim 10, wherein the baseline peripheral venous pressure frequency spectrum is obtained by:
    acquiring, by the IV device, the peripheral venous signals from the vein of the living subject at an earlier time period; and
    processing the peripheral venous signals acquired at the earlier time period by the spectral FFT analysis to obtain the baseline peripheral venous pressure frequency spectrum.

12. The system of claim 7, wherein the IV device further comprises:
- a port device in fluid communication with the tubing, located between the first and second ends of the tubing; and
- at least one pressure sensor in fluid communication with the tubing through the port device, configured to obtain the peripheral venous signals by measuring fluid pressures in the port device.

13. The system of claim 7, wherein the IV infiltration indicates occlusion or malposition of the IV catheter.

14. A method for monitoring an intravenous (IV) line functionality of an IV device, wherein the IV device comprises:
- an IV catheter, configured to be inserted into a vein of the living subject;
- a tubing having a first end and an opposite, second end, wherein the first end is connectable to a fluid source, and the second end is connected to the IV catheter; and
- a fluid controlling device in fluid communication with the tubing, located between the first and second ends of the tubing to control fluid flow from the fluid source to the IV catheter, the method comprising:
- acquiring, from the IV catheter, peripheral venous signals, wherein the IV catheter is configured to be inserted in the vein of the living subject;
- performing, by a processing device communicatively connected to the IV device, a spectral analysis on the acquired peripheral venous signals to obtain a peripheral venous pressure frequency spectrum;
- performing, by the processing device, a statistical analysis on amplitudes of peaks of the peripheral venous pressure frequency spectrum to determine the IV line functionality of the IV device in real time; and
- when the IV line functionality of the IV device is determined to indicate IV infiltration, controlling, by the processing device, the fluid controlling device to stop the fluid flow from the fluid source to the IV catheter.

15. The method of claim 14, wherein the spectral analysis is a spectral fast Fourier transform (FFT) analysis.

16. The method of claim 15, wherein the statistical analysis comprises:
- obtaining a plurality of baseline peaks $\{B_{N-1}\}$ on a baseline peripheral venous pressure frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$;
- obtaining a plurality of peaks $\{P_{N-1}\}$ on the peripheral venous pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and
- determining the IV line functionality of the IV device in real time by comparing the amplitudes of the peaks $\{P_{N-1}\}$ to that of the baseline peaks $\{B_{N-1}\}$ respectively.

17. The method of claim 15, wherein the baseline peripheral venous pressure frequency spectrum is obtained by:
- acquiring the peripheral venous signals from the IV catheter at an earlier time period; and
- processing the peripheral venous signals acquired at the earlier time period by the spectral FFT analysis to obtain the baseline peripheral venous pressure frequency spectrum.

18. The method of claim 14, wherein:
the IV line functionality of the IV device is determined to indicate IV infiltration when amplitude decreases greater than a first threshold are detected from the peaks of the peripheral venous pressure frequency spectrum.

19. The method of claim 18, wherein the IV infiltration indicates occlusion or malposition of the IV catheter.

20. The method of claim 14, wherein the IV device further comprises:
- a port device in fluid communication with the tubing, located between the first and second ends of the tubing; and
- at least one pressure sensor in fluid communication with the tubing through the port device, configured to obtain the peripheral venous signals by measuring fluid pressures in the port device.

21. The method of claim 14, wherein the processing device is a computing device.

* * * * *